(12) United States Patent
Chen et al.

(10) Patent No.: US 9,133,134 B2
(45) Date of Patent: Sep. 15, 2015

(54) INHIBITORS OF BRUTON'S TYROSINE KINASE

(71) Applicant: Pharmacyclics, Inc., Sunnyvale, CA (US)

(72) Inventors: Wei Chen, Fremont, CA (US); David J. Loury, San Jose, CA (US); Tarak D. Mody, Sunnyvale, CA (US)

(73) Assignee: PHARMACYCLICS LLC, Sunnyvale, CA (US)

( * ) Notice: Subject to any disclaimer, the term of this patent is extended or adjusted under 35 U.S.C. 154(b) by 0 days.

(21) Appl. No.: 14/401,104

(22) PCT Filed: May 15, 2013

(86) PCT No.: PCT/US2013/041242
§ 371 (c)(1),
(2) Date: Nov. 13, 2014

(87) PCT Pub. No.: WO2013/173518
PCT Pub. Date: Nov. 21, 2013

(65) Prior Publication Data
US 2015/0111912 A1    Apr. 23, 2015

Related U.S. Application Data

(60) Provisional application No. 61/647,956, filed on May 16, 2012.

(51) Int. Cl.
 *C07D 239/48* (2006.01)
 *A61K 31/505* (2006.01)

(52) U.S. Cl.
 CPC ............ *C07D 239/48* (2013.01); *A61K 31/505* (2013.01)

(58) Field of Classification Search
 CPC ............................ C07D 239/48; A61K 31/505
 USPC .......................................... 544/323; 514/275
 See application file for complete search history.

(56) References Cited

U.S. PATENT DOCUMENTS

| 8,329,901 | B2 | 12/2012 | Singh et al. |
| 8,338,439 | B2 | 12/2012 | Singh et al. |
| 8,445,798 | B2 | 5/2013 | Jiang et al. |
| 8,450,335 | B2 | 5/2013 | Singh et al. |
| 8,563,568 | B2 | 10/2013 | Witowski et al. |

FOREIGN PATENT DOCUMENTS

WO    WO 2011/090760    *    7/2011

* cited by examiner

*Primary Examiner* — Deepak Rao
(74) *Attorney, Agent, or Firm* — Wilson Sonsini Goodrich & Rosati

(57) ABSTRACT

Described herein are kinase inhibitor compounds, methods for synthesizing such inhibitors, and methods for using such inhibitors in the treatment of diseases. Further described herein are methods, assays and systems for determining an appropriate inhibitor of a protein, including a kinase.

19 Claims, No Drawings

INHIBITORS OF BRUTON'S TYROSINE KINASE

CROSS-REFERENCE

This application is a National Stage Entry of PCT/US2013/041242, filed May 15, 2013; which claims the benefit of U.S. provisional application Ser. No. 61/647,956, filed May 16, 2012, which is incorporated by reference in its entirety.

FIELD OF THE INVENTION

Described herein are kinase inhibitor compounds, methods for synthesizing such inhibitors, and methods for using such inhibitors in the treatment of diseases.

BACKGROUND OF THE INVENTION

A kinase, alternatively known as a phosphotransferase, is a type of enzyme that transfers phosphate groups from high-energy donor molecules, such as ATP, to specific target molecules; the process is termed phosphorylation. Protein kinases, which act on and modify the activity of specific proteins, are used to transmit signals and control complex processes in cells. Up to 518 different kinases have been identified in humans. Their enormous diversity and role in signaling makes them attractive targets for drug design.

SUMMARY OF THE INVENTION

Described herein are inhibitors of Bruton's tyrosine kinase (Btk). Also described herein are methods for synthesizing such inhibitors, methods for using such inhibitors in the treatment of diseases (including diseases wherein inhibition of Btk provides therapeutic benefit to a patient having the disease). Further described are pharmaceutical formulations that include an inhibitor of Btk.

In one aspect, provided herein are compounds of Formula (I) having the structure:

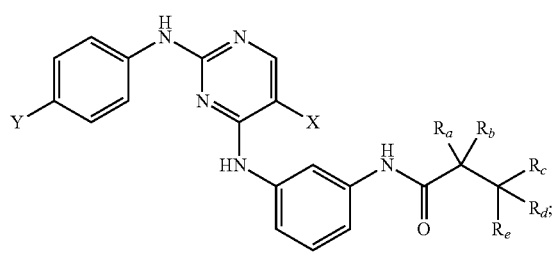

Formula (I)

wherein:
$R_a$, $R_b$, $R_c$, $R_d$ and $R_e$ are each independently selected from H, F, Cl, Br, I, —CN, —SR$_2$, —OR$_3$, —N(R$_3$)$_2$, and —CO$_2$R$_3$; or
$R_a$ or $R_b$ together with one of $R_c$, $R_d$ and $R_e$ and the carbon atoms to which they are attached form an epoxide; wherein $R_a$, $R_b$, $R_c$, $R_d$, and $R_e$ cannot all be H;
X is F, Cl, Br, I, or CF$_3$;
Y is F, Cl, Br, or I; or —OC$_1$-C$_2$alkyl optionally substituted with halogen or —OC$_1$-C$_2$alkyl; or an optionally substituted C$_2$-C$_5$heterocycle;
R$_2$ is selected from H, C$_1$-C$_4$alkyl, a cysteine amino acid fragment, and a glutathione fragment;
each R$_3$ is independently selected from H, C$_1$-C$_4$alkyl, phenyl, and benzyl;
or a pharmaceutically acceptable salt or solvate thereof.

In one embodiment is a compound of Formula (I) wherein $R_a$ is H. In another embodiment is a compound of Formula (I) wherein $R_b$ is —OR$_3$. In yet another embodiment is a compound of Formula (I) wherein $R_3$ is H. In a further embodiment is a compound of Formula (I) wherein at least two of $R_c$, $R_d$, and $R_e$ is H. In yet a further embodiment is a compound of Formula (I) wherein $R_c$ and $R_d$ are both H. In one embodiment is a compound of Formula (I) wherein $R_e$ is —OR$_3$. In another embodiment is a compound of Formula (I) wherein $R_3$ is H. In another embodiment is a compound of Formula (I) wherein $R_a$ and $R_b$ are both H. In yet another embodiment is a compound of Formula (I) wherein $R_a$ is H and $R_b$ is —OR$_3$. In a further embodiment is a compound of Formula (I) wherein $R_3$ is H. In yet a further embodiment is a compound of Formula (I) wherein $R_c$, $R_d$, and $R_e$ are each independently H. In one embodiment is a compound of Formula (I) wherein $R_a$ is H and $R_b$ is —OR$_3$. In another embodiment is a compound of Formula (I) wherein $R_3$ is H. In yet another embodiment is a compound of Formula (I) wherein $R_a$ or $R_b$ together with one of $R_c$, $R_d$ and $R_e$ and the carbon atoms to which they are attached form an epoxide.

In another aspect, provided herein are compounds of Formula (II) having the structure:

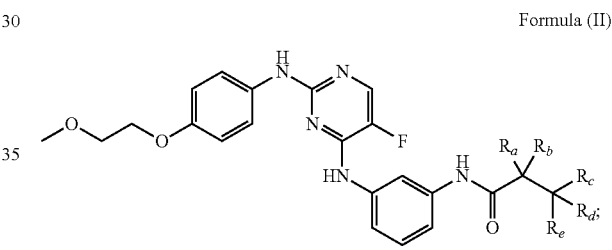

Formula (II)

wherein:
$R_a$, $R_b$, $R_c$, $R_d$ and $R_e$ are each independently selected from H, F, Cl, Br, I, —CN, —SR$_2$, —OR$_3$, —N(R$_3$)$_2$, and —CO$_2$R$_3$; or
$R_a$ or $R_b$ together with one of $R_c$, $R_d$ and $R_e$ and the carbon atoms to which they are attached form an epoxide; wherein $R_a$, $R_b$, $R_c$, $R_d$, and $R_e$ cannot all be H;
R$_2$ is selected from H, C$_1$-C$_4$alkyl, a cysteine amino acid fragment, and a glutathione fragment;
each R$_3$ is independently selected from H, C$_1$-C$_4$alkyl, phenyl, and benzyl;
or a pharmaceutically acceptable salt or solvate thereof.

In one embodiment is a compound having the structure

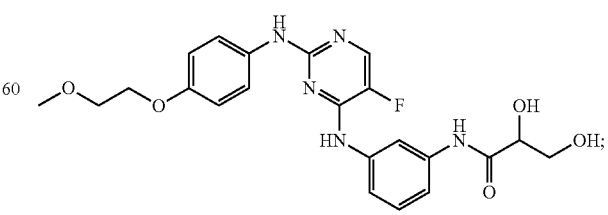

or a pharmaceutically acceptable salt or solvate thereof.

In one aspect is a pharmaceutical composition comprising a compound having the structure of Formula (I):

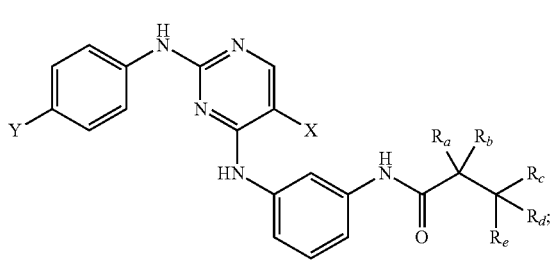

Formula (I)

wherein:
$R_a$, $R_b$, $R_c$, $R_d$ and $R_e$ are each independently selected from H, F, Cl, Br, I, —CN, —SR$_2$, —OR$_3$, —N(R$_3$)$_2$, and —CO$_2$R$_3$; or
$R_a$ or $R_b$ together with one of $R_c$, $R_d$ and $R_e$ and the carbon atoms to which they are attached form an epoxide; wherein $R_a$, $R_b$, $R_c$, $R_d$, and $R_e$ cannot all be H;
X is F, Cl, Br, I, or CF$_3$;
Y is F, Cl, Br, or I; or —OC$_1$-C$_2$alkyl optionally substituted with halogen or —OC$_1$-C$_2$alkyl; or an optionally substituted C$_2$-C$_5$heterocycle;
$R_2$ is selected from H, C$_1$-C$_4$alkyl, a cysteine amino acid fragment, and a glutathione fragment;
each $R_3$ is independently selected from H, C$_1$-C$_4$alkyl, phenyl, and benzyl;
or a pharmaceutically acceptable salt or solvate thereof; and a pharmaceutically acceptable excipient, binder or carrier.

In certain embodiments, provided herein is a pharmaceutical composition containing: i) a physiologically acceptable carrier, diluent, and/or excipient; and ii) one or more compounds provided herein.

In certain embodiments, the compound of Formula (I) is in an isolated form.

Other objects, features and advantages of the methods and compositions described herein will become apparent from the following detailed description. It should be understood, however, that the detailed description and the specific examples, while indicating specific embodiments, are given by way of illustration only. The section headings used herein are for organizational purposes only and are not to be construed as limiting the subject matter described.

DETAILED DESCRIPTION OF THE INVENTION

Certain Terminology

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Definition of standard chemistry terms are found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques are optionally used for chemical syntheses, chemical analyses, pharmaceutical preparation, formulation, and delivery, and treatment of patients. Standard techniques are optionally used for recombinant DNA, oligonucleotide synthesis, and tissue culture and transformation (e.g., electroporation, lipofection). Reactions and purification techniques are performed using documented methodologies or as described herein.

It is to be understood that the methods and compositions described herein are not limited to the particular methodology, protocols, cell lines, constructs, and reagents described herein and as such optionally vary. It is also to be understood that the terminology used herein is for the purpose of describing particular embodiments only, and is not intended to limit the scope of the methods and compositions described herein, which will be limited only by the appended claims.

An "alkyl" group refers to an aliphatic hydrocarbon group. The alkyl moiety includes a "saturated alkyl" group, which means that it does not contain any alkene or alkyne moieties. The alkyl moiety also includes an "unsaturated alkyl" moiety, which means that it contains at least one alkene or alkyne moiety. An "alkene" moiety refers to a group that has at least one carbon-carbon double bond, and an "alkyne" moiety refers to a group that has at least one carbon-carbon triple bond. The alkyl moiety, whether saturated or unsaturated, includes branched, straight chain, or cyclic moieties. Depending on the structure, an alkyl group includes a monoradical or a diradical (i.e., an alkylene group), and if a "lower alkyl" having 1 to 6 carbon atoms.

As used herein, C$_1$-C$_x$ includes C$_1$-C$_2$, C$_1$-C$_3$ ... C$_1$-C$_x$.

The "alkyl" moiety optionally has 1 to 10 carbon atoms (whenever it appears herein, a numerical range such as "1 to 10" refers to each integer in the given range; e.g., "1 to 10 carbon atoms" means that the alkyl group is selected from a moiety having 1 carbon atom, 2 carbon atoms, 3 carbon atoms, etc., up to and including 10 carbon atoms, although the present definition also covers the occurrence of the term "alkyl" where no numerical range is designated). The alkyl group of the compounds described herein may be designated as "C$_1$-C$_4$ alkyl" or similar designations. By way of example only, "C$_1$-C$_4$ alkyl" indicates that there are one to four carbon atoms in the alkyl chain, i.e., the alkyl chain is selected from among methyl, ethyl, propyl, iso-propyl, n-butyl, iso-butyl, sec-butyl, and t-butyl. Thus C$_1$-C$_4$ alkyl includes C$_1$-C$_2$ alkyl and C$_1$-C$_3$ alkyl. Alkyl groups are optionally substituted or unsubstituted. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like.

An "alkoxy" group refers to a (alkyl)O— group, where alkyl is as defined herein.

"Alkoxyalkyl" refers to an alkyl radical, as defined herein, substituted with an alkoxy group, as defined herein.

The term "amino acid fragment" refers to a portion of an amino acid, such as by way of example only, the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), or a dipeptide, tripeptide or other polypeptide comprising a combination of the 20 common amino acids or a non-natural amino acid. In some embodiments, the amino acid fragment is attached to the compound of Formula (I) via the side chain of the amino acid. In one embodiment, the amino acid fragment is a cysteine fragment wherein the remaining portion of the compound of Formula (I) is bound via a sulfur bond. In another embodiment, the amino acid fragment is a glutathione fragment wherein the remaining portion of a compound of Formula (I) is bound via a sulfur bond of the glutathione fragment. In another embodiment, the amino acid fragments are derived from beta-amino acids. In further embodiments, the amino acid fragments are derived from portions of polypeptides or proteins. In yet further embodiments, the amino acid fragment is attached to the compound of Formula (I) via the N-terminal or the acyl-terminal of the amino acid.

The term "ester" refers to a chemical moiety with formula —COOR$_3$, where R$_3$ is selected from among C$_1$-C$_4$alkyl, phenyl or benzyl. Any hydroxy, or carboxyl side chain on the compounds described herein can be esterified. The procedures and specific groups to make such esters are found in sources such as Greene and Wuts, Protective Groups in Organic Synthesis, 3$^{rd}$ Ed., John Wiley & Sons, New York, N.Y., 1999, which is incorporated herein by reference for this disclosure.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

The term "carbonyl" as used herein refers to a group containing a moiety selected from the group consisting of —C(O)—, —S(O)—, —S(O)$_2$—, and —C(S)—, including, but not limited to, groups containing a least one ketone group, and/or at least one aldehyde group, and/or at least one ester group, and/or at least one carboxylic acid group, and/or at least one thioester group. Such carbonyl groups include ketones, aldehydes, carboxylic acids, esters, and thioesters. In some embodiments, such groups are a part of linear, branched, or cyclic molecules.

The term "halo" or, alternatively, "halogen" or "halide" means fluoro, chloro, bromo and iodo.

The term "heteroatom" refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms can all be the same as one another, or some or all of the two or more heteroatoms can each be different from the others.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

A "thioalkoxy" or "alkylthio" group refers to a —S-alkyl group.

A "SH" group is also referred to either as a thiol group or a sulfhydryl group.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

As used herein, the term "agonist" refers to a compound, the presence of which results in a biological activity of a protein that is the same as the biological activity resulting from the presence of a naturally occurring ligand for the protein, such as, for example, Btk.

As used herein, the term "partial agonist" refers to a compound the presence of which results in a biological activity of a protein that is of the same type as that resulting from the presence of a naturally occurring ligand for the protein, but of a lower magnitude.

As used herein, the term "antagonist" refers to a compound, the presence of which results in a decrease in the magnitude of a biological activity of a protein. In certain embodiments, the presence of an antagonist results in complete inhibition of a biological activity of a protein, such as, for example, Btk. In certain embodiments, an antagonist is an inhibitor.

As used herein, "amelioration" of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

"Bioavailability" refers to the percentage of the weight of compounds disclosed herein, such as, compounds of Formula (I) or Formula (II), dosed that is delivered into the general circulation of the animal or human being studied. The total exposure (AUC$_{(0-\infty)}$) of a drug when administered intravenously is usually defined as 100% bioavailable (F %). "Oral bioavailability" refers to the extent to which compounds disclosed herein, such as, compounds of Formula (I) or Formula (II), are absorbed into the general circulation when the pharmaceutical composition is taken orally as compared to intravenous injection.

"Blood plasma concentration" refers to the concentration of compounds disclosed herein, such as, compounds of Formula (I) or Formula (II), in the plasma component of blood of a subject. It is understood that the plasma concentration of compounds of Formula (I) or Formula (II), may vary significantly between subjects, due to variability with respect to metabolism and/or possible interactions with other therapeutic agents. In accordance with one embodiment disclosed herein, the blood plasma concentration of the compounds of Formula (I) or Formula (II), does vary from subject to subject. Likewise, values such as maximum plasma concentration (C$_{max}$) or time to reach maximum plasma concentration (T$_{max}$), or total area under the plasma concentration time curve (AUC$_{(0-\infty)}$) may vary from subject to subject. Due to this variability, the amount necessary to constitute "a therapeutically effective amount" of a compound of Formula (I) or Formula (II) is expected to vary from subject to subject.

The term "Bruton's tyrosine kinase," as used herein, refers to Bruton's tyrosine kinase from *Homo sapiens*, as disclosed in, e.g., U.S. Pat. No. 6,326,469 (GenBank Accession No. NP_000052).

The term "Bruton's tyrosine kinase homolog," as used herein, refers to orthologs of Bruton's tyrosine kinase, e.g., the orthologs from mouse (GenBank Accession No.

AAB47246), dog (GenBank Accession No. XP_549139.), rat (GenBank Accession No. NP_001007799), chicken (GenBank Accession No. NP_989564), or zebra fish (GenBank Accession No. XP_698117), and fusion proteins of any of the foregoing that exhibit kinase activity towards one or more substrates of Bruton's tyrosine kinase (e.g. a peptide substrate having the amino acid sequence "AVLESEEELYS-SARQ").

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case is optionally determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of the compound of Formula (I) or Formula (II), age, weight, general condition of the subject, the condition being treated, the severity of the condition being treated, and the judgment of the prescribing physician.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder or condition. An "enhancing-effective amount," as used herein, refers to an amount adequate to enhance the effect of a therapeutic agent in the treatment of a disease, disorder or condition. When used in a patient, amounts effective for this use will depend on the severity and course of the disease, disorder or condition, previous therapy, the patient's health status and response to the drugs, and the judgment of the treating physician.

The term "homologous cysteine," as used herein refers to a cysteine residue found with in a sequence position that is homologous to that of cysteine 481 of Bruton's tyrosine kinase, as defined herein. For example, cysteine 482 is the homologous cysteine of the rat ortholog of Bruton's tyrosine kinase; cysteine 479 is the homologous cysteine of the chicken ortholog; and cysteine 481 is the homologous cysteine in the zebra fish ortholog. In another example, the homologous cysteine of TXK, a Tec kinase family member related to Bruton's tyrosine, is Cys 350. See also the sequence alignments of tyrosine kinases (TK) published on the world wide web at kinase.com/human/kinome/phylogeny.html.

The terms "inhibits", "inhibiting", or "inhibitor" of a kinase, as used herein, refer to inhibition of enzymatic phosphotransferase activity.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

The term "plasma half life," as used herein refers to half-life in rat, dog or human as determined by measure drug concentration over time in plasma following a single dose and fitting data to standard pharmacokinetic models using software such as WinNonLin to determine the time at which drug has been 50% eliminated from plasma.

The term "prophylactically effective amount," as used herein, refers that amount of a composition applied to a patient which will relieve to some extent one or more of the symptoms of a disease, condition or disorder being treated. In such prophylactic applications, such amounts may depend on the patient's state of health, weight, and the like.

As used herein, the term "selective binding compound" refers to a compound that selectively binds to any portion of one or more target proteins.

As used herein, the term "selectively binds" refers to the ability of a selective binding compound to bind to a target protein, such as, for example, Btk, with greater affinity than it binds to a non-target protein. In certain embodiments, specific binding refers to binding to a target with an affinity that is at least about 10, about 50, about 100, about 250, about 500, about 1000 or more times greater than the affinity for a non-target.

As used herein, the term "selective modulator" refers to a compound that selectively modulates a target activity relative to a non-target activity. In certain embodiments, specific modulator refers to modulating a target activity at least about 10, about 50, about 100, about 250, about 500, about 1000 times more than a non-target activity.

The term "substantially purified," as used herein, refers to a component of interest that may be substantially or essentially free of other components which normally accompany or interact with the component of interest prior to purification. By way of example only, a component of interest may be "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, a "substantially purified" component of interest may have a purity level of about 70%, about 75%, about 80%, about 85%, about 90%, about 95%, about 96%, about 97%, about 98%, about 99% or greater.

The term "subject" as used herein, refers to an animal which is the object of treatment, observation or experiment. By way of example only, a subject may be, but is not limited to, a mammal including, but not limited to, a human.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

As used herein, the term "target protein" refers to a molecule or a portion of a protein capable of being bound by a selective binding compound. In certain embodiments, a target protein is Btk.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

As used herein, the $IC_{50}$ refers to an amount, concentration or dosage of a particular test compound that achieves a 50% inhibition of a maximal response, such as inhibition of Btk, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

Inhibitor Compounds

In the following description of kinase inhibitor compounds suitable for use in the methods described herein. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients.

In one aspect, provided herein are compounds of Formula (I) having the structure:

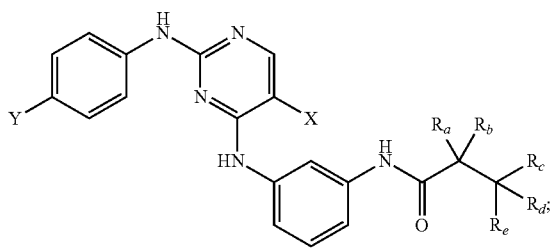

Formula (I)

wherein:

$R_a$, $R_b$, $R_c$, $R_d$ and $R_e$ are each independently selected from H, F, Cl, Br, I, —CN, —SR$_2$, —OR$_3$, —N(R$_3$)$_2$, and —CO$_2$R$_3$; or $R_a$ or $R_b$ together with one of $R_c$, $R_d$ and $R_e$ and the carbon atoms to which they are attached form an epoxide; wherein $R_a$, $R_b$, $R_c$, $R_d$, and $R_e$ cannot all be H;

X is F, Cl, Br, I, or CF$_3$;

Y is F, Cl, Br, or I; or —OC$_1$-C$_2$alkyl optionally substituted with halogen or —OC$_1$-C$_2$alkyl;

or an optionally substituted C$_2$-C$_5$heterocycle;

$R_2$ is selected from H, C$_1$-C$_4$alkyl, a cysteine amino acid fragment, and a glutathione fragment;

each $R_3$ is independently selected from H, C$_1$-C$_4$alkyl, phenyl, and benzyl;

or a pharmaceutically acceptable salt or solvate thereof.

In one embodiment is a compound of Formula (I) wherein X is F, Cl, Br, I, or CF$_3$. In some embodiments, X is F. In some embodiments, X is Cl. In some embodiments, X is Br. In some embodiments, X is I. In some embodiments, X is CF$_3$. In another embodiment is a compound of Formula (I) wherein Y is F, Cl, Br, or I; or —OC$_1$-C$_2$alkyl optionally substituted with halogen or —OC$_1$-C$_2$alkyl; or an optionally substituted C$_2$-C$_5$heterocycle. In some embodiments is a compound of Formula (I) wherein Y is F, Cl, Br, or I. In some embodiments, Y is F. In some embodiments, Y is Cl. In some embodiments, Y is Br. In some embodiments, Y is I. In other embodiments is a compound of Formula (I) wherein Y is —OC$_1$-C$_2$alkyl optionally substituted with halogen or —OC$_1$-C$_2$alkyl. In some embodiments, Y is —OCH$_3$. In some embodiments, Y is —OCH$_2$CH$_3$. In some embodiments, Y is —OCH$_2$CH$_2$OCH$_3$. In another embodiment is a compound of Formula (I) wherein Y is an optionally substituted C$_2$-C$_5$heterocycle. In another embodiment is a compound of Formula (I) wherein X is F and Y is —OCH$_3$. In another embodiment is a compound of Formula (I) wherein X is F and Y is —OCH$_2$CH$_3$. In another embodiment is a compound of Formula (I) wherein X is F and Y is —OCH$_2$CH$_2$OCH$_3$. In another embodiment is a compound of Formula (I) wherein X is Cl and Y is —OCH$_3$. In another embodiment is a compound of Formula (I) wherein X is Cl and Y is —OCH$_2$CH$_3$. In another embodiment is a compound of Formula (I) wherein X is Cl and Y is —OCH$_2$CH$_2$OCH$_3$.

In another embodiment is a compound of Formula (I) wherein $R_a$, $R_b$, $R_c$, $R_d$ and $R_e$ are each independently selected from H, F, Cl, Br, I, —CN, —SR$_2$, —OR$_3$, —N(R$_3$)$_2$, and —CO$_2$R$_3$. In another embodiment is a compound of Formula (I) wherein $R_a$ is H. In another embodiment is a compound of Formula (I) wherein $R_b$ is —OR$_3$. In yet another embodiment is a compound of Formula (I) wherein $R_3$ is H. In a further embodiment is a compound of Formula (I) wherein at least two of $R_c$, $R_d$, and $R_e$ is H. In yet a further embodiment is a compound of Formula (I) wherein $R_c$ and $R_d$ are both H. In one embodiment is a compound of Formula (I) wherein $R_e$ is —OR$_3$. In another embodiment is a compound of Formula (I) wherein $R_3$ is H. In another embodiment is a compound of Formula (I) wherein $R_a$ and $R_b$ are both H. In another embodiment is a compound of Formula (I) wherein $R_a$, $R_b$, $R_c$, $R_d$ are H and $R_e$ is —SR$_2$. In another embodiment is a compound of Formula (I) wherein $R_a$, $R_b$, $R_c$, $R_d$ are H, $R_e$ is —SR$_2$, and $R_2$ is a cysteine amino acid fragment. In another embodiment is a compound of Formula (I) wherein $R_a$, $R_b$, $R_c$, $R_d$ are H, $R_e$ is —SR$_2$, and $R_2$ is a glutathione fragment. In another embodiment is a compound of Formula (I) wherein $R_a$ is H and $R_b$ is —OR$_3$. In another embodiment is a compound of Formula (I) wherein $R_a$ is H and $R_b$ is —OH. In yet a further embodiment is a compound of Formula (I) wherein $R_c$, $R_d$, and $R_e$ are each independently H. In one embodiment is a compound of Formula (I) wherein $R_a$ is H and $R_b$ is —OR$_3$. In another embodiment is a compound of Formula (I) wherein $R_3$ is H. In another embodiment is a compound of Formula (I) wherein $R_a$, $R_c$, $R_d$, and $R_e$ are each H and $R_b$ is —OH. In another embodiment is a compound of Formula (I) wherein $R_a$, $R_b$, $R_c$, and $R_d$ are each H and $R_e$ is —OH. In another embodiment is a compound of Formula (I) wherein $R_a$, $R_c$, $R_d$ are each H and $R_b$ and $R_e$ are each —OH. In yet another embodiment is a compound of Formula (I) wherein $R_a$ or $R_b$ together with one of $R_c$, $R_d$ and $R_e$ and the carbon atoms to which they are attached form an epoxide.

In one embodiment is a compound of Formula (I) having the structure:

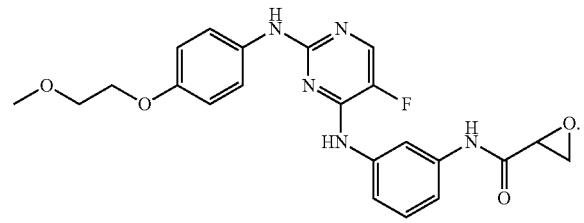 [SMILES: COCCOc1ccc(Nc2ncc(F)c(Nc3cccc(NC(=O)C4CO4)c3)n2)cc1]

In another aspect, provided herein are compounds of Formula (II) having the structure:

Formula (II)

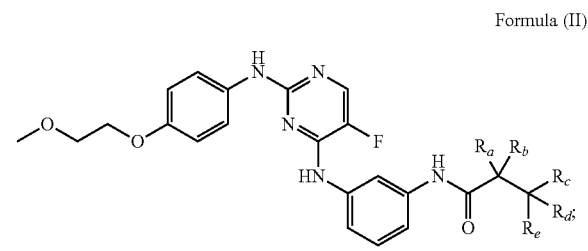

wherein:

$R_a$, $R_b$, $R_c$, $R_d$ and $R_e$ are each independently selected from H, F, Cl, Br, I, —CN, —SR$_2$, —OR$_3$, —N(R$_3$)$_2$, and —CO$_2$R$_3$; or $R_a$ or $R_b$ together with one of $R_c$, $R_d$ and $R_e$ and the carbon atoms to which they are attached form an epoxide; wherein $R_a$, $R_b$, $R_c$, $R_d$, and $R_e$ cannot all be H;

$R_2$ is selected from H, $C_1$-$C_4$alkyl, a cysteine amino acid fragment, and a glutathione fragment;

each $R_3$ is independently selected from H, $C_1$-$C_4$alkyl, phenyl, and benzyl;

or a pharmaceutically acceptable salt or solvate thereof.

In another embodiment is a compound of Formula (II) wherein $R_a$, $R_b$, $R_c$, $R_d$ and $R_e$ are each independently selected from H, F, Cl, Br, I, —CN, —SR$_2$, —OR$_3$, —N(R$_3$)$_2$, and —CO$_2$R$_3$. In another embodiment is a compound of Formula (II) wherein $R_a$ is H. In another embodiment is a compound of Formula (II) wherein $R_b$ is —OR$_3$. In yet another embodiment is a compound of Formula (II) wherein $R_3$ is H. In a further embodiment is a compound of Formula (II) wherein at least two of $R_c$, $R_d$, and $R_e$ is H. In yet a further embodiment is a compound of Formula (II) wherein $R_c$ and $R_d$ are both H. In one embodiment is a compound of Formula (II) wherein $R_e$ is —OR$_3$. In another embodiment is a compound of Formula (II) wherein $R_3$ is H. In another embodiment is a compound of Formula (II) wherein $R_a$ and $R_b$ are both H. In another embodiment is a compound of Formula (II) wherein $R_a$, $R_b$, $R_c$, $R_d$ are H and $R_e$ is —SR$_2$. In another embodiment is a compound of Formula (II) wherein $R_a$, $R_b$, $R_c$, $R_d$ are H, $R_e$ is —SR$_2$, and $R_2$ is a cysteine amino acid fragment. In another embodiment is a compound of Formula (II) wherein $R_a$, $R_b$, $R_c$, $R_d$ are H, $R_e$ is —SR$_2$, and $R_2$ is a glutathione fragment. In another embodiment is a compound of Formula (II) wherein $R_a$ is H and $R_b$ is —OR$_3$. In another embodiment is a compound of Formula (II) wherein $R_a$ is H and $R_b$ is —OH. In yet a further embodiment is a compound of Formula (II) wherein $R_c$, $R_d$, and $R_e$ are each independently H. In one embodiment is a compound of Formula (II) wherein $R_a$ is H and $R_b$ is —OR$_3$. In another embodiment is a compound of Formula (II) wherein $R_3$ is H. In another embodiment is a compound of Formula (II) wherein $R_a$, $R_c$, $R_d$, and $R_e$ are each H and $R_b$ is —OH. In another embodiment is a compound of Formula (II) wherein $R_a$, $R_b$, $R_c$, and $R_d$ are each H and $R_e$ is —OH. In another embodiment is a compound of Formula (II) wherein $R_a$, $R_c$, $R_d$ are each H and $R_b$ and $R_e$ are each —OH. In yet another embodiment is a compound of Formula (II) wherein $R_a$ or $R_b$ together with one of $R_c$, $R_d$ and $R_e$ and the carbon atoms to which they are attached form an epoxide.

In one aspect, provided herein is a compound selected from among:

N-(3-(5-fluoro-2-(4-(2-methoxyethoxy)phenylamino)pyrimidin-4-ylamino)phenyl)-2,3-dihydroxypropanamide,
N-(3-(5-fluoro-2-(4-(2-methoxyethoxy)phenylamino)pyrimidin-4-ylamino)phenyl)-3-hydroxypropanamide,
N-(3-(5-fluoro-2-(4-(2-methoxyethoxy)phenylamino)pyrimidin-4-ylamino)phenyl)-2-hydroxypropanamide,
N-(3-(5-fluoro-2-(4-(2-methoxyethoxy)phenylamino)pyrimidin-4-ylamino)phenyl)oxirane-2-carboxamide, and
(S)-2-amino-5-((R)-1-(carboxymethylamino)-3-(3-(3-(5-fluoro-2-(4-(2-methoxyethoxy)phenylamino)pyrimidin-4-ylamino)phenylamino)-3-oxopropylthio)-1-oxopropan-2-ylamino)-5-oxopentanoic acid; or a pharmaceutically acceptable salt, solvate or tautomeric form thereof.

In some embodiments, the inhibitors described herein are used for the manufacture of a medicament for treating any of the foregoing conditions (e.g., autoimmune diseases, inflammatory diseases, allergy disorders, B-cell proliferative disorders, or thromboembolic disorders).

In some embodiments, the inhibitor compound used for the methods described herein inhibits a kinase activity with an in vitro $IC_{50}$ of less than about 10 µM. (e.g., less than about 1 µM, less than about 0.5 µM, less than about 0.4 µM, less than about 0.3 µM, less than about 0.1, less than about 0.08 µM, less than about 0.06 µM, less than about 0.05 µM, less than about 0.04 µM, less than about 0.03 µM, less than about 0.02 µM, less than about 0.01, less than about 0.008 µM, less than about 0.006 µM, less than about 0.005 µM, less than about 0.004 µM, less than about 0.003 µM, less than about 0.002 µM, less than about 0.001, less than about 0.00099 µM, less than about 0.00098 µM, less than about 0.00097 µM, less than about 0.00096 µM, less than about 0.00095 µM, less than about 0.00094 µM, less than about 0.00093 µM, less than about 0.00092, or less than about 0.00090 µM).

In one embodiment, the inhibitor compound selectively inhibits an activated form of its target tyrosine kinase (e.g., a phosphorylated form of the tyrosine kinase). For example, activated Btk is transphosphorylated at tyrosine 551. Thus, in these embodiments the Btk inhibitor inhibits the target kinase in cells only once the target kinase is activated by the signaling events.

Preparation of Compounds

Compounds of any of Formula (I) or Formula (II) are optionally synthesized using standard synthetic techniques or using such methods known in combination with methods described herein. In additions, solvents, temperatures and other reaction conditions are presented herein for illustration only, and not to limit the scope of the methods and compositions described herein. As a further guide the following synthetic methods may also be utilized.

The reactions are optionally employed in a linear sequence to provide the compounds described herein or used to synthesize fragments which are subsequently joined by the methods described herein and/or documented elsewhere.

Formation of Covalent Linkages by Reaction of an Electrophile with a Nucleophile The compounds described herein can be modified using various electrophiles or nucleophiles to form new functional groups or substituents. Table 1 entitled "Examples of Covalent Linkages and Precursors Thereof" lists selected examples of covalent linkages and precursor functional groups which yield and can be used as guidance toward the variety of electrophiles and nucleophiles combinations available. Precursor functional groups are shown as electrophilic groups and nucleophilic groups.

TABLE 1

Examples of Covalent Linkages and Precursors Thereof

| Covalent Linkage Product | Electrophile | Nucleophile |
|---|---|---|
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |
| Alkyl thiol | α,β-unsaturated ester | thiols |
| Alkyl ethers | α,β-unsaturated ester | alcohols |
| Alkyl amines | α,β-unsaturated ester | amines |
| Alkyl thiol | Vinyl sulfone | thiols |
| Alkyl ethers | Vinyl sulfone | alcohols |
| Alkyl amines | Vinyl sulfone | amines |
| Vinyl sulfide | Propargyl amide | thiol |

Use of Protecting Groups

In the reactions described, it may be necessary to protect reactive functional groups, for example hydroxy, amino, imino, thio or carboxy groups, where these are desired in the final product, to avoid their unwanted participation in the reactions. Protecting groups are used to block some or all reactive moieties and prevent such groups from participating in chemical reactions until the protective group is removed. In one embodiment, each protective group can be removable by a different means. Protective groups that are cleaved under totally disparate reaction conditions fulfill the requirement of differential removal. Protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a Pd⁰-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

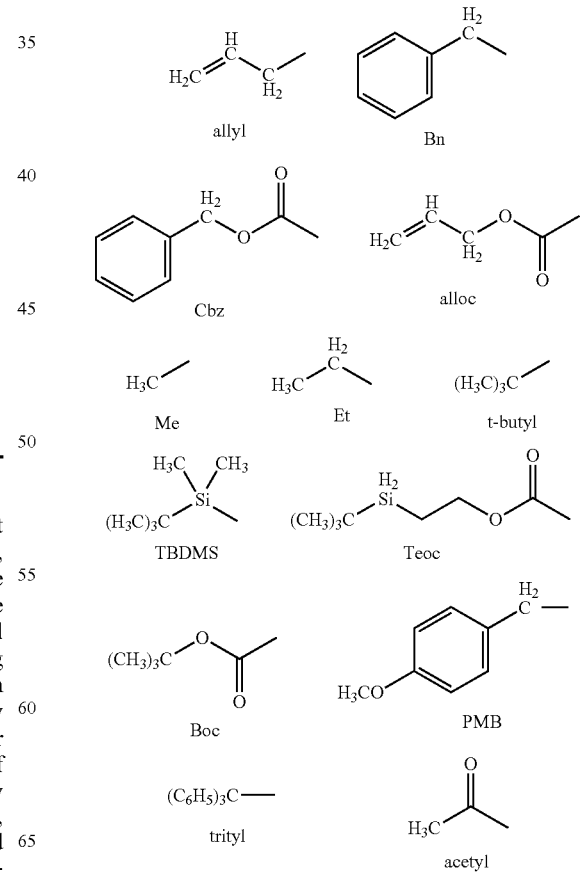

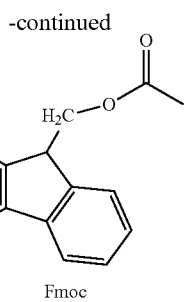

Fmoc

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Synthesis of Compounds

In certain embodiments, provided herein are methods of making the tyrosine kinase inhibitor compounds described herein. In certain embodiments, compounds described herein are synthesized using the following synthetic schemes. In other embodiments, compounds are synthesized using methodologies analogous to those described below by the use of appropriate alternative starting materials.

The starting material used for the synthesis of the compounds described herein is either synthesized or obtained from commercial sources, such as, but not limited to, Aldrich Chemical Co. (Milwaukee, Wis.), Bachem (Torrance, Calif.), or Sigma Chemical Co. (St. Louis, Mo.). The compounds described herein, and other related compounds having different substituents are optionally synthesized using techniques and materials, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001); Green and Wuts, PROTECTIVE GROUPS IN ORGANIC SYNTHESIS 3$^{rd}$ Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989). Other methods for the synthesis of compounds described herein may be found in International Patent Publication No. WO 01/01982901, Arnold et al. *Bioorganic & Medicinal Chemistry Letters* 10 (2000) 2167-2170; Burchat et al. *Bioorganic & Medicinal Chemistry Letters* 12 (2002) 1687-1690. As a guide the following synthetic methods may be utilized.

The products of the reactions are optionally isolated and purified, if desired, using conventional techniques, including, but not limited to, filtration, distillation, crystallization, chromatography and the like. Such materials are optionally characterized using conventional means, including physical constants and spectral data.

Compounds described herein are optionally prepared using the synthetic methods described herein as a single isomer or a mixture of isomers.

A non-limiting example of a synthetic approach towards the preparation of a compound of Formula (I) is shown in Scheme I.

Scheme I

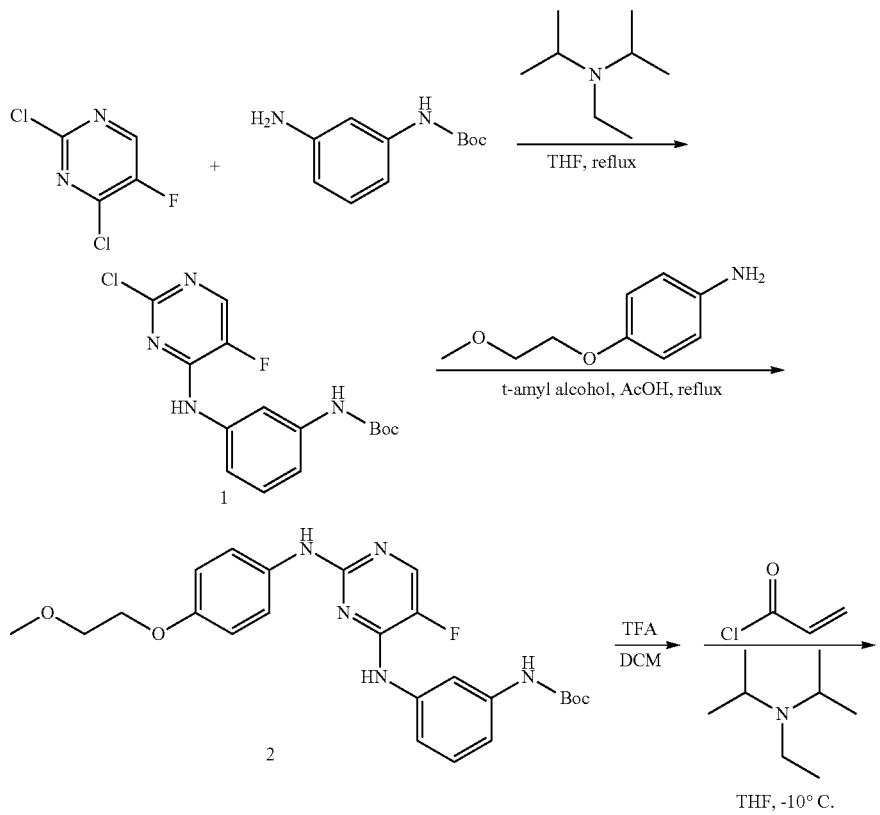

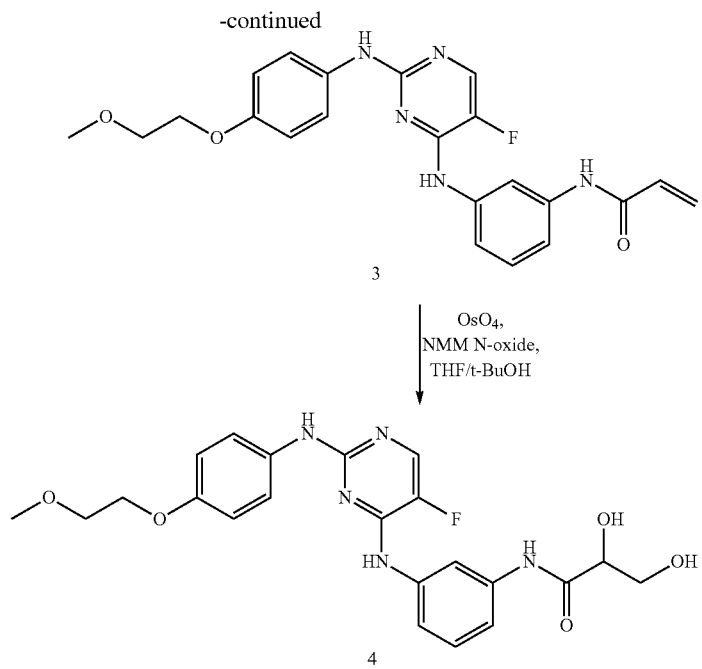

In one embodiment, 2,4-dichloro-5-fluoropyrimidine, t-butyl 3-aminophenylcarbamate, and Hunig's base are heated at reflux in THF to give 1. Coupling of 1 and 4-(2-methoxyethoxy)aniline in the presence of catalytic acetic acid in t-amyl alcohol at reflux affords 2. Following removal of the Boc protecting group, the deprotected amine is acylated with acryloyl chloride to give 3. Dihydroxylation of 3 with osmium tetroxide in t-BuOH affords diol 4.

The compounds prepared by the methods disclosed herein are purified by conventional means, such as, for example, filtration, recrystallization, chromatography, distillation, and combinations thereof.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

Further Forms of Compounds

Compounds disclosed herein have a structure of Formula (I) or Formula (II). It is understood that when reference is made to compounds described herein, it is meant to include compounds of any of Formula (I) or Formula (II), as well as to all of the specific compounds that fall within the scope of these generic formulae, unless otherwise indicated.

In some embodiments, the compounds described herein possess one or more stereocenters and in further embodiments, each center exists in the R or S configuration. The compounds presented herein include all diastereomeric, enantiomeric, and epimeric forms as well as the appropriate mixtures thereof. In other embodiments, stereoisomers are obtained, if desired, by methods such as, for example, the separation of stereoisomers by chiral chromatographic columns.

In further embodiments, diastereomeric mixtures are separated into their individual diastereomers on the basis of their physical chemical differences by methods known, for example, by chromatography and/or fractional crystallization. In one embodiment, enantiomers can be separated by chiral chromatographic columns. In other embodiments, enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers, and mixtures thereof are considered as part of the compositions described herein.

The methods and formulations described herein include the use of N-oxides, crystalline forms (also known as polymorphs), or pharmaceutically acceptable salts of compounds described herein. In some situations, compounds exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

In some embodiments, compounds of Formula (I) or Formula (II) in unoxidized form are prepared from N-oxides of compounds of any of Formula (I) or Formula (II) by treating with a reducing agent, such as, but not limited to, sulfur, sulfur dioxide, triphenyl phosphine, lithium borohydride, sodium borohydride, phosphorus trichloride, tribromide, or the like in a suitable inert organic solvent, such as, but not limited to, acetonitrile, ethanol, aqueous dioxane, or the like at 0 to 80° C.

Compounds described herein include isotopically-labeled compounds, which are identical to those recited in the various formulas and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^{2}H$, $^{3}H$, $^{13}C$, $^{14}C$, $^{15}N$, $^{18}O$, $^{17}O$, $^{35}S$, $^{18}F$, $^{36}Cl$ respectively. Certain isotopically-labeled compounds described herein, for example those into which radioactive isotopes such as $^3H$ and $^{14}C$ are incorporated, are useful in drug and/or substrate tissue distribution assays. Further, substitution with isotopes such as deuterium, i.e., $^2H$, can afford certain therapeutic advantages resulting from greater metabolic stability, for example increased in vivo half-life or reduced dosage requirements.

In one embodiment is an isolated and/or pure form of a compound of Formula (I) or Formula (II). In another embodiment, is a compound of Formula (I) or Formula (II) wherein the compound is at least about 40% pure. In another embodiment, is a compound of Formula (I) or Formula (II) wherein the compound is at least about 50%, about 60%, about 70%, about 80%, about 90%, about 95% pure. In yet another embodiment is a compound of Formula (I) or Formula (II) in an isolated form. In yet another embodiment, is a compound of Formula (I) or Formula (II) wherein the compound is purified by chromatography.

Compounds described herein (for example, compounds of Formula (I) or Formula (II)) are optionally in the form of, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; (2) salts formed when an acidic proton present in the parent compound either is replaced by a metal ion, e.g., an alkali metal ion (e.g. lithium, sodium, potassium), an alkaline earth ion (e.g. magnesium, or calcium), or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts are optionally analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by using at least one of the following techniques: filtration, precipitation with a non-solvent followed by filtration, evaporation of the solvent, or, in the case of aqueous solutions, lyophilization.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are optionally formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization with pharmaceutically acceptable solvents such as water, ethanol, and the like. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Compounds described herein are optionally in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UVIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Therapeutic Uses of Inhibitor Compounds

In one aspect, provided herein are methods for treating a patient by administering a compound provided herein. In some embodiments, provided herein is a method of inhibiting the activity of tyrosine kinase(s), such as Btk, or of treating a disease, disorder, or condition, which benefit from inhibition of tyrosine kinase(s), such as Btk, in a patient, which includes administering to the patient a therapeutically effective amount of at least one of any of the compounds described herein, or pharmaceutically acceptable salt, pharmaceutically acceptable tautomer, pharmaceutically acceptable prodrug, or pharmaceutically acceptable solvate.

In another aspect, provided herein is the use of a compound disclosed herein for inhibiting Bruton's tyrosine kinase (Btk) activity or for the treatment of a disease, disorder, or condition, which benefit from inhibition of Bruton's tyrosine kinase (Btk) activity.

In some embodiments, compounds provided herein are administered to a human. In some embodiments, compounds provided herein are orally administered. In other embodiments, the pharmaceutical formulation that is formulated for a route of administration is selected from oral administration, parenteral administration, buccal administration, nasal administration, topical administration, or rectal administration.

In other embodiments, compounds provided herein are used for the formulation of a medicament for the inhibition of tyrosine kinase activity. In some other embodiments, compounds provided herein are used for the formulation of a medicament for the inhibition of Bruton's tyrosine kinase (Btk) activity.

In a further aspect, provided herein is a method for treating an autoimmune disease by administering to a subject in need thereof a composition containing a therapeutically effective amount of at least one compound having the structure of Formula (I) or Formula (II). In one embodiment, the autoimmune disease is arthritis. In another embodiment, the autoimmune disease is lupus. In some embodiments, the autoimmune disease is inflammatory bowel disease (including Crohn's disease and ulcerative colitis), rheumatoid arthritis, psoriatic arthritis, osteoarthritis, Still's disease, juvenile arthritis, lupus, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystis, neuromyotonia, scleroderma, or vulvodynia.

In a further aspect, provided herein is a method for treating a heteroimmune condition or disease by administering to a subject in need thereof a composition containing a therapeutically effective amount of at least one compound having the structure of Formula (I) or Formula (II). In some embodiments, the heteroimmune condition or disease is graft versus host disease, transplantation, transfusion, anaphylaxis, allergy, type I hypersensitivity, allergic conjunctivitis, allergic rhinitis, or atopic dermatitis.

In a further aspect, provided herein is a method for treating an inflammatory disease by administering to a subject in need thereof a composition containing a therapeutically effective amount of at least one compound having the structure of Formula (I) or Formula (II). In some embodiments, the inflammatory disease is asthma, inflammatory bowel disease (including Crohn's disease and ulcerative colitis), appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In yet another aspect, provided herein is a method for treating a cancer by administering to a subject in need thereof a composition containing a therapeutically effective amount of at least one compound having the structure of Formula (I) or Formula (II). In one embodiment, the cancer is a B-cell proliferative disorder, e.g., diffuse large B cell lymphoma, follicular lymphoma, chronic lymphocytic lymphoma, chronic lymphocytic leukemia, B-cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt's lymphoma/leukemia, or lymphomatoid granulomatosis. In some embodiments, where the subject is suffering from a cancer, an anti-cancer agent is administered to the subject in addition to one of the above-mentioned compounds. In one embodiment, the anti-cancer agent is an inhibitor of mitogen-activated protein kinase signaling, e.g., U0126, PD98059, PD184352, PD0325901, ARRY-142886, SB239063, SP600125, BAY 43-9006, wortmannin, or LY294002.

In another aspect, provided herein is a method for treating a thromboembolic disorder by administering to a subject in need thereof a composition containing a therapeutically effective amount of at least one compound having the structure of Formula (I) or Formula (II). In some embodiments, the thromboembolic disorder is myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In another aspect, provided herein is a method for treating a mastocytosis by administering to a subject in need thereof a composition containing a therapeutically effective amount of at least one compound having the structure of Formula (I) or Formula (II).

In yet another aspect, provided herein is a method for treating an osteoporosis or bone resorption disorders by administering to a subject in need thereof a composition containing a therapeutically effective amount of at least one compound having the structure of Formula (I) or Formula (II).

Also described herein are kinase inhibitors that selectively bind to a protein tyrosine kinase selected from Btk, a Btk homolog, and a Btk kinase cysteine homolog, in which the kinase inhibitor reversibly and non-selectively binds to a multiplicity of protein tyrosine kinases. In one embodiment the plasma half life of the kinase inhibitor is less than about 4 hours. In another embodiment the plasma half life of the kinase inhibitor is less than about 3 hours.

In a further embodiment are kinase inhibitors that selectively bind to at least one of Btk, Jak3, Blk, Bmx, Tec, and Itk. In another embodiment are kinase inhibitors that selectively bind to Btk. In another embodiment are kinase inhibitors that selectively bind to Jak3. In another embodiment are kinase inhibitors that selectively bind to Tec. In another embodiment are kinase inhibitors that selectively bind to Itk. In another embodiment are kinase inhibitors that selectively bind to Btk and Tec. In another embodiment are kinase inhibitors that selectively bind to Blk. In yet a further embodiment are kinase inhibitors that reversibly and non-selectively bind to a multiplicity of src-family protein kinase inhibitors.

Also described herein are inhibitors that are identified using such methods, assays and systems. In some embodiments, the inhibitor is a selective inhibitor, including selectivity for a particular Btk kinase cysteine homolog over other Btk kinase cysteine homologs.

Further described herein are pharmaceutical formulations comprising the kinase inhibitors of any kinase inhibitor compound previously listed. In one embodiment the pharmaceutical formulation includes a pharmaceutical acceptable excipient. In some embodiments, pharmaceutical formulations provided herein are administered to a human. In some embodiments, the selective kinase inhibitors provided herein are orally administered. In other embodiments, the selective kinase inhibitors provided herein are used for the formulation of a medicament for the inhibition of tyrosine kinase activity. In some other embodiments, the selective kinase inhibitors provided herein are used for the formulation of a medicament for the inhibition of a kinase activity, including a tyrosine kinase activity, including a Btk activity, including a Btk homolog activity, including a Btk kinase cysteine homolog activity.

In any of the aforementioned aspects are further embodiments in which administration is enteral, parenteral, or both, and wherein (a) the effective amount of the compound is systemically administered to the mammal; (b) the effective amount of the compound is administered orally to the mammal; (c) the effective amount of the compound is intravenously administered to the mammal; (d) the effective amount of the compound administered by inhalation; (e) the effective amount of the compound is administered by nasal administration; or (f) the effective amount of the compound is administered by injection to the mammal; (g) the effective amount of the compound is administered topically (dermal) to the mammal; (h) the effective amount of the compound is administered by ophthalmic administration; or (i) the effective amount of the compound is administered rectally to the mammal. In further embodiments the pharmaceutical formulation is formulated for a route of administration selected from oral administration, parenteral administration, buccal administration, nasal administration, topical administration, or rectal administration.

In any of the aforementioned aspects are further embodiments comprising single administrations of the effective amount of the pharmaceutical formulation, including further embodiments in which (i) the pharmaceutical formulations is administered once; (ii) the pharmaceutical formulations is administered to the mammal once a day; (iii) the pharmaceutical formulations is administered to the mammal multiple times over the span of one day; (iv) continually; or (v) continuously.

In any of the aforementioned aspects are further embodiments comprising multiple administrations of the effective amount of the pharmaceutical formulations, including further embodiments in which (i) the pharmaceutical formulations is administered in a single dose; (ii) the time between multiple administrations is every 6 hours; (iii) the pharmaceutical formulations is administered to the mammal every 8 hours. In further or alternative embodiments, the method comprises a drug holiday, wherein the administration of the pharmaceutical formulations is temporarily suspended or the dose of the pharmaceutical formulations being administered is temporarily reduced; at the end of the drug holiday, dosing of the pharmaceutical formulations is resumed. The length of the drug holiday varies from 2 days to 1 year.

In some aspects described herein the inhibitor is selective for one kinase selected from Btk, a Btk homolog, and a Btk kinase cysteine homolog over at least one other kinase selected from Btk, a Btk homolog, and a Btk kinase cysteine homolog. In other aspects described herein the inhibitor is selective for at least one kinase selected from Btk, a Btk homolog, and a Btk kinase cysteine homolog over at least one other non-kinase molecule having an accessible SH group.

Described herein are methods, compositions, uses and medicaments for the treatment of disorders comprising administering to a patient in need an inhibitor of an ACK. In some embodiments, the ACK is Btk or a Btk homolog. In further embodiments, the ACK is Blk or a Blk homolog. In yet further embodiments, the ACK is tyrosine kinases that share homology with Btk by having a cysteine residue (including a Cys 481 residue) that can form a bond with the inhibitor.

The methods described herein (which includes uses of a pharmaceutical composition to treat a disease or disorder, or uses of a compound to form a medicament for treating a disease or disorder) include administering to a subject in need a composition containing a therapeutically effective amount of one or more Btk inhibitor compounds described herein. Without being bound by theory, the diverse roles played by Btk signaling in various hematopoietic cell functions, e.g., B-cell receptor activation, show that small molecule Btk inhibitors are useful for reducing the risk of or treating a variety of diseases affected by or affecting many cell types of the hematopoietic lineage including, e.g., autoimmune diseases, heteroimmune conditions or diseases, inflammatory diseases, cancer (e.g., B-cell proliferative disorders), and thromboembolic disorders.

In some embodiments, are methods for treating an autoimmune disease or condition comprising administering to a patient in need a pharmaceutical formulation of any inhibitor of Btk (or a Btk homolog) of Formula (I) or Formula (II). Such an autoimmune disease or condition includes, but is not limited to, rheumatoid arthritis, psoriatic arthritis, osteoarthritis, Still's disease, juvenile arthritis, lupus, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, and vulvodynia. In some embodiments, the autoimmune disease is selected from rheumatoid arthritis or lupus.

In some embodiments, are methods for treating a heteroimmune disease or condition comprising administering to a patient in need a pharmaceutical formulation of any inhibitor of Btk (or a Btk homolog) of Formula (I) or Formula (II). Such a heteroimmune condition or disease includes, but is not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In some embodiments, are methods for treating a cancer comprising administering to a patient in need a pharmaceutical formulation of any inhibitor of Btk (or a Btk homolog) of Formula (I) or Formula (II). Such a cancer, e.g., B-cell proliferative disorders, includes but is not limited to diffuse large B cell lymphoma, follicular lymphoma, chronic lymphocytic lymphoma, chronic lymphocytic leukemia, B-cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, and lymphomatoid granulomatosis.

In some embodiments, are methods for treating mastocytosis comprising administering to a patient in need a pharmaceutical formulation of any inhibitor of Btk (or a Btk homolog) of Formula (I) or Formula (II). Mastocytosis includes but is not limited to diseases characterized by hyperactive mast cells.

In some embodiments, are methods for treating osteoporosis or bone resorption disorders comprising administering to a patient in need a pharmaceutical formulation of any inhibitor of Btk (or a Btk homolog) of Formula (I) or Formula (II). Bone resorption disorders include but are not limited to Paget's disease of bone, osteoporosis, and the bone changes secondary to cancer, such as occur in myeloma and metastases from breast cancer.

In some embodiments, are methods for treating inflammatory diseases comprising administering to a patient in need a pharmaceutical formulation of any inhibitor of Btk (or a Btk homolog) of Formula (I) or Formula (II). Inflammatory diseases include but are not limited to asthma, inflammatory bowel disease, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, and vulvitis.

A subset of tyrosine kinases other than Btk are also expected to be useful as therapeutic targets in a number of health conditions, including:

autoimmune diseases, which include, but are not limited to, rheumatoid arthritis, psoriatic arthritis, osteoarthritis, Still's disease, juvenile arthritis, lupus, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, and vulvodynia.

heteroimmune conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

inflammatory diseases, which include, but are not limited to asthma, inflammatory bowel disease, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, and vulvitis.

a cancer, e.g., B-cell proliferative disorders, which include, but are not limited to diffuse large B cell lymphoma, follicular lymphoma, chronic lymphocytic lymphoma, chronic lymphocytic leukemia, B-cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, and lymphomatoid granulomatosis.

thromboembolic disorders, which include, but are not limited to myocardial infarct, angina pectoris (including unstable angina), reocclusions or restenoses after angioplasty or aortocoronary bypass, stroke, transitory ischemia, peripheral arterial occlusive disorders, pulmonary embolisms, and deep venous thromboses.

mastocytosis, which include but are not limited to diseases characterized by hyperactive mast cells.

bone resorption disorders, which include but are not limited to Paget's disease of bone, osteoporosis, and the bone changes secondary to cancer, such as occur in myeloma and metastases from breast cancer.

Symptoms, diagnostic tests, and prognostic tests for each of the above-mentioned conditions include, e.g., *Harrison's Principles of Internal Medicine©*," 16th ed., 2004, The McGraw-Hill Companies, Inc. Dey et al. (2006), Cytojournal 3(24), and the "Revised European American Lymphoma" (REAL) classification system (see, e.g., the website maintained by the National Cancer Institute).

A number of animal models are useful for establishing a range of therapeutically effective doses of inhibitors, including Btk inhibitor compounds for treating any of the foregoing diseases. Also, for example, dosing of inhibitor compounds for treating an autoimmune disease can be assessed in a mouse model of rheumatoid arthritis. In this model, arthritis is induced in Balb/c mice by administering anti-collagen antibodies and lipopolysaccharide. See Nandakumar et al. (2003), *Am. J. Pathol* 163:1827-1837. In another example, dosing of inhibitors for the treatment of B-cell proliferative disorders can be examined in, e.g., a human-to-mouse xenograft model in which human B-cell lymphoma cells (e.g. Ramos cells) are implanted into immunodefficient mice (e.g., "nude" mice) as described in, e.g., Pagel et al. (2005), Clin Cancer Res 11(13):4857-4866. Animal models for treatment of thromboembolic disorders are also known.

In one embodiment, the therapeutic efficacy of the compound for one of the foregoing diseases is optimized during a course of treatment. For example, a subject being treated optionally undergoes a diagnostic evaluation to correlate the relief of disease symptoms or pathologies to inhibition of in vivo Btk activity achieved by administering a given dose of a Btk inhibitor. Cellular assays are used to determine in vivo activity of Btk in the presence or absence of a Btk inhibitor. For example, since activated Btk is phosphorylated at tyrosine 223 (Y223) and tyrosine 551 (Y551), phospho-specific immunocytochemical staining of P-Y223 or P-Y551-positive cells are used to detect or quantify activation of Btk in a population of cells (e.g., by FACS analysis of stained vs unstained cells). See, e.g., Nisitani et al. (1999), *Proc. Natl. Acad. Sci, USA* 96:2221-2226. Thus, the amount of the Btk inhibitor compound that is administered to a subject is optionally increased or decreased as needed so as to maintain a level of Btk inhibition optimal for treating the subject's disease state.

Combination Treatments

In some embodiments, the Btk inhibitor compositions described herein are used in combination with other well known therapeutic reagents that are selected for their therapeutic value for the condition to be treated. In general, the compositions described herein and, in embodiments where combinational therapy is employed, other agents do not have to be administered in the same pharmaceutical composition, and are optionally, because of different physical and chemical characteristics, have to be administered by different routes. The initial administration is made, for example, according to established protocols, and then, based upon the observed effects, the dosage, modes of administration and times of administration are modified.

In certain instances, it is appropriate to administer at least one Btk inhibitor compound described herein in combination with another therapeutic agent. By way of example only, if one of the side effects experienced by a patient upon receiving one of the Btk inhibitor compounds described herein is nausea, then it is appropriate to administer an anti-nausea agent in combination with the initial therapeutic agent. Or, by way of example only, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, by way of example only, the benefit experienced by a patient is increased by administering one of the compounds described herein with another therapeutic agent (which also includes a therapeutic regimen) that also has therapeutic benefit. In any case, regardless of the disease, disorder or condition being treated, the overall benefit experienced by the patient is in some embodiments simply additive of the two therapeutic agents or in other embodiments, the patient experiences a synergistic benefit.

The particular choice of compounds used will depend upon the diagnosis of the attending physicians and their judgment of the condition of the patient and the appropriate treatment protocol. The compounds are optionally administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is based on an evaluation of the disease being treated and the condition of the patient.

Therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is a compound of Formula (I) or Formula (II) described herein) are optionally administered in any order or even simultaneously. If simultaneously, the multiple therapeutic agents are optionally provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the compounds described herein also are optionally used in combination with procedures that provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

In some embodiments, the compounds described herein and combination therapies are administered before, during or after the occurrence of a disease or condition, and the timing of administering the composition containing a compound can vary. Thus, for example, the compounds can be used as a prophylactic and can be administered continuously to subjects with a propensity to develop conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, within the first 6 hours of the onset of the symptoms, or within 3 hours of the onset of the symptoms. The initial administration can be via any route practical, such as, for example, an intravenous injection, a bolus injection, infusion over 5 minutes to about 5 hours, a pill, a capsule, transdermal patch, buccal delivery, and the like, or combination thereof. A compound should be administered as soon as is practicable after the onset of a disease or condition is detected or suspected, and for a length of time necessary for the treatment of the disease, such as, for example, from about 1 month to about 3 months. The length of treatment can vary for each subject, and the length can be determined using the known criteria. For example, the compound or a formulation containing the compound can be administered for at least 2 weeks, between about 1 month to about 5 years, or from about 1 month to about 3 years.

Therapeutic Agents for Use in Combination with an Inhibitor Compound

In some embodiments, where the subject is suffering from or at risk of suffering from an autoimmune disease, an inflammatory disease, or an allergy disease, a Btk inhibitor compound is used in with one or more of the following therapeutic agents in any combination: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-α binding proteins (e.g., infliximab, etanercept, or adalimumab), abatacept, anakinra, interferon-β, interferon-γ, interleukin-2, allergy vaccines, antihistamines, antileukotrienes, beta-agonists, theophylline, anticholinergics or other selective kinase inhibitors (e.g p38 inhibitors, Syk inhibitors, PKC inhibitors).

In yet other embodiments, where the subject is suffering from or at risk of suffering from a B-cell proliferative disorder (e.g., plasma cell myeloma), the subjected is treated with a Btk inhibitor compound in any combination with one or more other anti-cancer agents. In some embodiments, one or more of the anti-cancer agents are proapoptotic agents. Examples of anti-cancer agents include, but are not limited to, any of the following: gossyphol, oblimersen sodium, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib, geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with an Btk inhibitor compound include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

In further embodiments, other anti-cancer agents are employed in combination with an Btk inhibitor compound include doxorubicin, dactinomycin, bleomycin, vinblastine, cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or r1L2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

In yet other embodiments, other anti-cancer agents are employed in combination with an Btk inhibitor compound include: 20-epi-1,25 dihydroxyvitamin D3; 5-ethynyl uracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; 4-ipomeanol; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapaz amine; titanocene bichloride; topsentin; toremifene; totipotent stem cell factor; translation inhibitors; tretinoin; triacetyluridine;

triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a Btk inhibitor compound include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with a Btk inhibitor compound include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that are employed in combination a Btk inhibitor compound in some embodiments, include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Examples of hormones and antagonists useful in combination with a Btk inhibitor compound include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol (DES), ethinyl estradiol, antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which are used in some embodiments, in combination with a Btk inhibitor compound include without limitation marketed drugs and drugs in development.

Where the subject is suffering from or at risk of suffering from a thromboembolic disorder (e.g., stroke), the subject, in some embodiments is treated with a Btk inhibitor compound in any combination with one or more other anti-thromboembolic agents. Examples of anti-thromboembolic agents include, but are not limited any of the following: thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), factor VIIa inhibitors, ticlopidine, clopidogrel, CS-747 (prasugrel, LY640315), ximelagatran, or BIBR 1048.

Pharmaceutical Composition/Formulation

In a further aspect are provided pharmaceutical compositions, which include a therapeutically effective amount of at least one of any of the compounds described herein, or a pharmaceutically acceptable salt, pharmaceutically acceptable tautomer, pharmaceutically acceptable prodrug, or pharmaceutically acceptable solvate. In certain embodiments, compositions provided herein further include a pharmaceutically acceptable diluent, excipient and/or binder.

Pharmaceutical compositions formulated for administration by an appropriate route and means containing effective concentrations of one or more of the compounds provided herein, or pharmaceutically effective derivatives thereof, that deliver amounts effective for the treatment, prevention, or amelioration of one or more symptoms of diseases, disorders or conditions that are modulated or otherwise affected by tyrosine kinase activity, or in which tyrosine kinase activity is implicated, are provided. The effective amounts and concentrations are effective for ameliorating any of the symptoms of any of the diseases, disorders or conditions disclosed herein.

Pharmaceutical compositions are formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein is found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery* Systems, Seventh Ed. (Lippincott Williams & Wilkins 1999).

A pharmaceutical composition, as used herein, refers to a mixture of a compound described herein, such as, for example, compounds of any of Formula (I) or Formula (II), with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. Preferably, the mammal is a human. The compounds, in some embodiments, are used singly or in combination with one or more therapeutic agents as components of mixtures.

The pharmaceutical formulations described herein in some embodiments, is administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein are optionally manufactured in a conventional manner, such as, by way of example only, by means of conventional mixing, dissolving, granulating, dragee-making, levigating, emulsifying, encapsulating, entrapping or compression processes.

A "carrier" or "carrier materials" includes excipients in pharmaceutics and is selected on the basis of compatibility with compounds disclosed herein, such as, compounds of Formula (I) or Formula (II), and the release profile properties of the desired dosage form. Exemplary carrier materials include, e.g., binders, suspending agents, disintegration agents, filling agents, surfactants, solubilizers, stabilizers, lubricants, wetting agents, diluents, and the like. See, e.g., *Remington: The Science and Practice of Pharmacy*, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

A "measurable serum concentration" or "measurable plasma concentration" describes the blood serum or blood plasma concentration, typically measured in mg, µg, or ng of therapeutic agent per ml, dl, or l of blood serum, absorbed into the bloodstream after administration. As used herein, measurable plasma concentrations are typically measured in ng/ml or µg/ml.

"Pharmacodynamics" refers to the factors which determine the biologic response observed relative to the concentration of drug at a site of action. "Pharmacokinetics" refers to the factors which determine the attainment and maintenance of the appropriate concentration of drug at a site of action.

"Steady state," as used herein, is when the amount of drug administered is equal to the amount of drug eliminated within one dosing interval resulting in a plateau or constant plasma drug exposure.

Dosage Forms

Moreover, the pharmaceutical compositions described herein, which include a compound of Formula (I) or Formula (II) are, in some embodiments, formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

The pharmaceutical solid dosage forms described herein optionally include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences*, 20th Edition (2000), a film coating is provided around the formulation of the compound of Formula (I) or Formula (II). In one embodiment, some or all of the particles of the compound of Formula (I) or Formula (II), are coated. In another embodiment, some or all of the particles of the compound of Formula (I) or Formula (II), are microencapsulated. In still another embodiment, the particles of the compound of Formula (I) or Formula (II), are not microencapsulated and are uncoated.

Examples of Methods of Dosing and Treatment Regimens

The compounds described herein, in some embodiments, is used in the preparation of medicaments for the inhibition of Btk or a homolog thereof, or for the treatment of diseases or conditions that benefit, at least in part, from inhibition of Btk or a homolog thereof. In addition, a method for treating any of the diseases or conditions described herein in a subject in need of such treatment, involves administration of pharmaceutical compositions containing at least one compound of any of Formula (I) or Formula (II), described herein, or a pharmaceutically acceptable salt, pharmaceutically acceptable N-oxide, or pharmaceutically acceptable solvate thereof, in therapeutically effective amounts to said subject.

The compositions containing the compound(s) described herein, in other embodiments, are administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In some embodiments, the kinase inhibitor is administered to the patient on a regular basis, e.g., three times a day, two times a day, once a day, every other day or every 3 days. In other embodiments, the kinase inhibitor is administered to the patient on an intermittent basis, e.g., twice a day followed by once a day followed by three times a day; or the first two days of every week; or the first, second and third day of a week. In some embodiments, intermittent dosing is as effective as regular dosing. In further or alternative embodiments, the kinase inhibitor is administered only when the patient exhibits a particular symptom, e.g., the onset of pain, or the onset of a fever, or the onset of an inflammation, or the onset of a skin disorder.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from about 10%-about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, and is determined according to the particular circumstances surrounding the case, including, e.g., the specific agent being administered, the route of administration, the condition being treated, and the subject or host being treated. In general, however, doses employed for adult human treatment will typically be in the range of about 0.02-about 5000 mg per day, or from about 1-about 1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Kits/Articles of Manufacture

Articles of manufacture including packaging material, a compound or composition or pharmaceutically acceptable derivative thereof provided herein, which is effective for inhibiting the activity of tyrosine kinase(s), such as Btk, within the packaging material, and a label that indicates that the compound or composition, or pharmaceutically acceptable salt, pharmaceutically acceptable tautomer, pharmaceutically acceptable prodrug, or pharmaceutically acceptable solvate thereof, is used for inhibiting the activity of tyrosine kinase(s), such as Btk, are provided.

EXAMPLES

The following specific and non-limiting examples are to be construed as merely illustrative, and do not limit the present disclosure in any way whatsoever.

Example 1

Synthesis of N-(3-(5-fluoro-2-(4-(2-methoxyethoxy) phenylamino)pyrimidin-4-ylamino)phenyl)-2,3-dihydroxypropanamide (4)

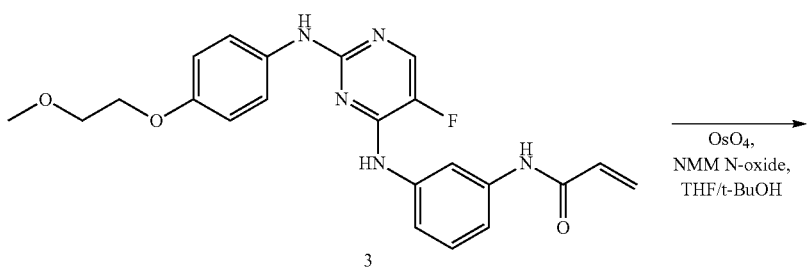

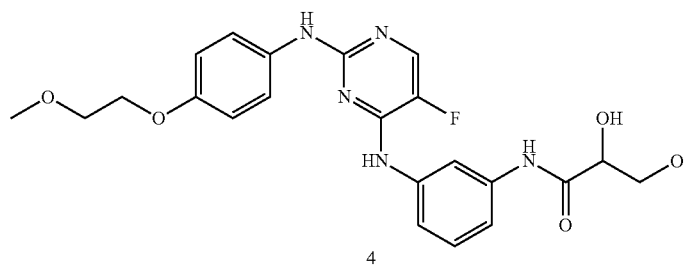

To a mixture of N-(3-{5-fluoro-2-[4-(2-methoxy-ethoxy)-phenylamino]-pyrimidin-4-ylamino}-phenyl)-acrylamide 3 (0.2 g, 0.47 mmol) and NMM N-oxide (0.2 g, 1.71 mmol) in THF (10 mL) and t-BuOH (10 mL) was added $OsO_4$ (0.2 g) at 0° C. The resulting mixture was stirred at room temperature for 24 h and then $Na_2S_2O_4$ (1 g) was added. The mixture was stirred at room temperature for 16 h and then concentrated. The residue was subjected to FCC (5% $CH_3OH/DCM$) to afford the title compound, N-(3-(5-fluoro-2-(4-(2-methoxyethoxy)phenylamino)pyrimidin-4-ylamino)phenyl)-2,3-dihydroxypropanamide (0.18 g, 83%).

Example 2

Synthesis of (S)-2-amino-5-((R)-1-(carboxymethylamino)-3-(3-(3-(5-fluoro-2-(4-(2-methoxyethoxy)phenylamino)pyrimidin-4-ylamino)phenylamino)-3-oxopropylthio)-1-oxopropan-2-ylamino)-5-oxopentanoic acid (5)

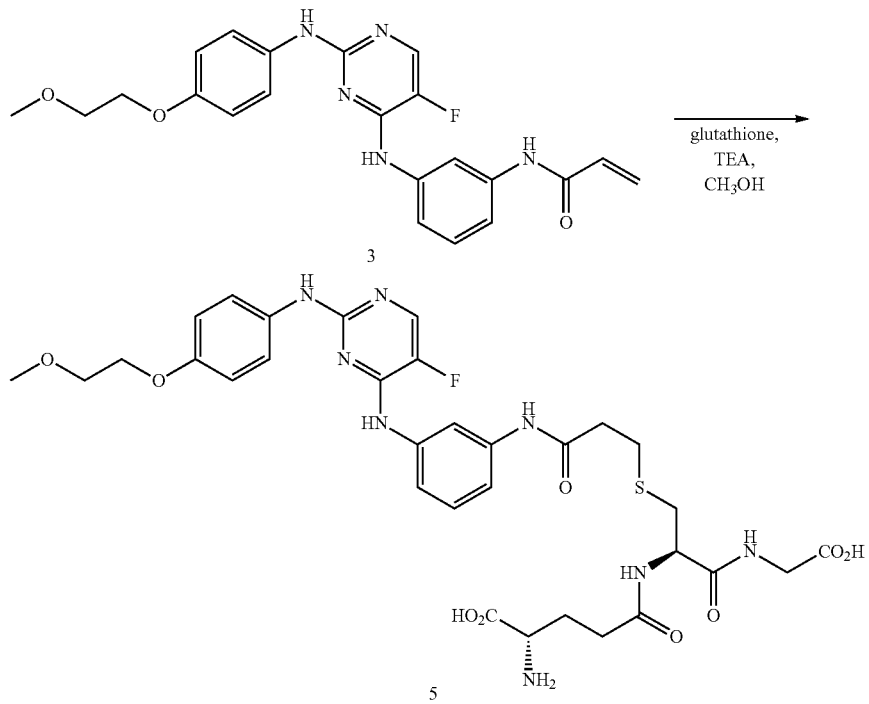

To a suspension of N-(3-{5-fluoro-2-[4-(2-methoxyethoxy)-phenylamino]-pyrimidin-4-ylamino}-phenyl)-acrylamide 3 (0.1 g, 0.236 mmol) and glutathione (0.1 g, 0.325 mmol) in DCM (10 mL) and $CH_3OH$ (10 mL) was added TEA (0.1 g, 0.988 mmol) dropwise at 0° C. The resulting mixture was stirred at room temperature for 16 h and then concentrated. The residue was washed with $H_2O$ and dried to afford the title compound, (S)-2-amino-5-((R)-1-(carboxymethylamino)-3-(3-(3-(5-fluoro-2-(4-(2-methoxyethoxy)phenylamino)pyrimidin-4-ylamino)phenylamino)-3-oxopropylthio)-1-oxopropan-2-ylamino)-5-oxopentanoic acid (0.17 g, 100%).

Example 3

Inhibition of Btk

The Btk $IC_{50}$s of compounds disclosed herein is determined in enzymatic kinase assay as described below.

Kinase activity is measured in vitro using electrophoretic mobility shift assay. The kinase reactions are assembled in a total volume of 25 μL in 384 well plates. The reactions comprise: BTK enzyme (1 nM, N-terminal His6-tagged, recombinant, full-length, human BTK purified from baculovirus Sf21 insect cell system), inhibitor, ATP (16 μM, the apparent $K_m$ for the kinase), fluorescently labeled peptide substrate (1 μM, FAM-GEEPLYWSFPAKKK-NH2) in a reaction buffer composed of 100 mM HEPES, pH7.5, 5 mM $MgCl_2$ 1 mM DTT, 0.1% bovine serum albumin, 0.01% Triton X-100, and 1% DMSO. The reaction is incubated for one hour and is quenched by the addition of 45 μL of termination buffer (100 mM HEPES, pH7.5, 0.01% Triton X-100, 30 mM EDTA). The terminated reactions are analyzed using 12 channel LabChip® 3000 microfluidic detection instrument (Caliper Life Sciences). The enzymatic phosphorylation of the peptide results in a change in net charge, enabling electrophoretic separation of product from substrate peptide. As substrate and product peptides are separated, two peaks of fluorescence are observed. Change in the relative fluorescence intensity of the substrate and product peaks is the parameter measured, reflecting enzyme activity. In the presence of an inhibitor, the ratio between product and substrate is altered: the signal of the product decreases, while the signal of the substrate increases.

Activity in each sample is determined as the product to sum ratio (PSR): P/(S+P), where P is the peak height of the product peptide and S is the peak height of the substrate peptide. For each compound, enzyme activity is measured at various concentrations (12 concentrations of compound spaced by 3× dilution intervals). Negative control samples (0%-inhibition in the absence of inhibitor) and positive control samples (100%-inhibition, in the presence of 20 mM EDTA) are assembled in replicates of four and are used to calculate %-inhibition values for each inhibitor at each concentration. Percent inhibition ($P_{inh}$) is determined using following equation:

$P_{inh}=(PSR_{0\%}-PSR_{inh})/(PSR_{0\%}-PSR_{100\%})*100$, where $PSR_{inh}$ is the product sum ratio in the presence of inhibitor, $PSR_{0\%}$ is the average product sum ration in the absence of inhibitor and $PSR_{100\%}$ is the average product sum ratio in 100%-inhibition control samples;

The $IC_{50}$ values of inhibitors are determined by 4 parameter sigmoidal dose-response model fitting of the inhibition curves ($P_{inh}$ versus inhibitor concentration) using XLfit 4 software.

| Compound | BTK IC50 |
|---|---|
| 4 | <500 nM |

The properties of the compounds disclosed herein are further characterized by assaying a number of cellular biochemical and functional endpoints to assess the selectivity of these compounds for inhibition of Btk versus the closely related protein kinases Lck, Lyn, and Syk. In anti-IgM-stimulated Ramos cells (a human B cell line), are assayed Btk-dependent phosphorylation of PLC-γ1; Lyn and Syk-dependent phosphorylation of tyrosine 551 on Btk; and BCR-activated calcium flux. The effect of compounds disclosed herein on Jurkat cells are measured wherein a human T cell line in which Lck and Itk, but not Btk are required for T cell receptor mediated $Ca^{2+}$ flux.

Example 4

Use of a Compound of Formula (I) or Formula (II) to Treat Rheumatoid Arthritis

The in vivo efficacy of the compounds described herein are evaluated in a mouse model of rheumatoid arthritis. Arthritis is induced in Balb/c mice by administration of anti-collagen antibodies and lipopolysaccharide (LPS). See Nandakumar et al. (2003), *Am. J. Pathol.* 163:1827-1837. Female Balb/c mice are treated with 100 mg/kg of Chemicon mAb cocktail to Type II collagen intravenously on Day 0 and 1.25 mg/kg of LPS intraperitoneally on Day 1. A test compound is administered orally in a methylcellulose-based aqueous suspension formulation at 1, 3, 10 and 30 mg/kg once daily starting on Day 2 through Day 12. Blood samples are collected at 0.5 and 2 hours post dose of the test compound administration on Day 12. The serum concentrations of the test compound are quantified by LC/MS/MS. Twenty four hours post dose, levels of the test compound below the level of quantitation.

Example 5

Inhibition of Mast Cell Degranulation

Human CD34+ cells differentiated to mast cells by 9 weeks in culture in the presence of 1 ng/ml IL-3, 50 ng/ml IL-6, 100 ng/ml SCF. Cells are incubated with IgE+IL-4 for 4 days and then degranulation is induced by cross-linking with anti-IgE. Degranulation quantitated using hexosaminidase assay. The $IC_{50}$ in MC degranulation of the compounds are determined. Compounds with desired $IC_{50}$ values are used for the treatment of inflammatory diseases, such as asthma.

Example 6

Pharmaceutical Compositions

The compositions described below are presented with a compound of Formula (I) or Formula (II) for illustrative purposes; any of the compounds of any of Formula (I) or Formula (II) are optionally used in such pharmaceutical compositions.

Example 6a

Parenteral Composition

To prepare a parenteral pharmaceutical composition suitable for administration by injection, 100 mg of a water-soluble salt of a compound of Formula (I) or Formula (II) is dissolved in DMSO and then mixed with 10 mL of 0.9% sterile saline. The mixture is incorporated into a dosage unit form suitable for administration by injection.

Example 6b

Oral Composition

To prepare a pharmaceutical composition for oral delivery, 100 mg of a compound of Formula (I) or Formula (II) is mixed with 750 mg of starch. The mixture is incorporated into an oral dosage unit for, such as a hard gelatin capsule, which is suitable for oral administration.

Example 6c

Sublingual (Hard Lozenge) Composition

To prepare a pharmaceutical composition for buccal delivery, such as a hard lozenge, mix 100 mg of a compound of Formula (I) or Formula (II), with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 6d

Inhalation Composition

To prepare a pharmaceutical composition for inhalation delivery, 20 mg of a compound of Formula (I) or Formula (II) is mixed with 50 mg of anhydrous citric acid and 100 mL of 0.9% sodium chloride solution. The mixture is incorporated into an inhalation delivery unit, such as a nebulizer, which is suitable for inhalation administration.

Example 6e

Rectal Gel Composition

To prepare a pharmaceutical composition for rectal delivery, 100 mg of a compound of Formula (I) or Formula (II) is mixed with 2.5 g of methylcellulose (1500 mPa), 100 mg of methylparaben, 5 g of glycerin and 100 mL of purified water. The resulting gel mixture is then incorporated into rectal delivery units, such as syringes, which are suitable for rectal administration.

Example 6f

Topical Gel Composition

To prepare a pharmaceutical topical gel composition, 100 mg of a compound of Formula (I) or Formula (II) is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Example 6g

Ophthalmic Solution Composition

To prepare a pharmaceutical ophthalmic solution composition, 100 mg of a compound of Formula (I) or Formula (II) is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

What is claimed is:

1. A compound having the structure of Formula (I):

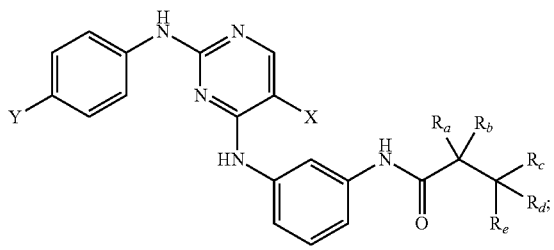

Formula (I)

wherein:
$R_a$, $R_b$, $R_c$, $R_d$ and $R_e$ are each independently selected from H, F, Cl, Br, I, —CN, —$SR_2$, —$OR_3$, —$N(R_3)_2$, and —$CO_2R_3$; or
$R_a$ or $R_b$ together with one of $R_c$, $R_d$ and $R_e$ and the carbon atoms to which they are attached form an epoxide; wherein $R_a$, $R_b$, $R_c$, $R_d$, and $R_e$ cannot all be H;
X is F, Cl, Br, I, or $CF_3$;
Y is F, Cl, Br, or I; or —$OC_1$-$C_2$alkyl optionally substituted with halogen or —$OC_1$-$C_2$alkyl; or an optionally substituted $C_2$-$C_5$heterocycle;
$R_2$ is selected from H, $C_1$-$C_4$alkyl, a cysteine amino acid fragment, and a glutathione fragment;
each $R_3$ is independently selected from H, $C_1$-$C_4$alkyl, phenyl, and benzyl;
or a pharmaceutically acceptable salt or solvate thereof.

2. The compound of claim 1 wherein $R_a$ is H.
3. The compound of claim 2 wherein $R_b$ is —$OR_3$.
4. The compound of claim 3 wherein $R_3$ is H.
5. The compound of claim 1 wherein at least two of $R_c$, $R_d$, and $R_e$ are H.
6. The compound of claim 5 wherein $R_c$ and $R_d$ are both H.
7. The compound of claim 6 wherein $R_e$ is —$OR_3$.
8. The compound of claim 7 wherein $R_3$ is H.
9. The compound of claim 8 wherein $R_a$ and $R_b$ are both H.
10. The compound of claim 8 wherein $R_a$ is H and $R_b$ is —$OR_3$.
11. The compound of claim 10 wherein $R_3$ is H.
12. The compound of claim 5 wherein $R_c$, $R_d$, and $R_e$ are each independently H.
13. The compound of claim 12 wherein $R_a$ is H and $R_b$ is —$OR_3$.
14. The compound of claim 13 wherein $R_3$ is H.
15. The compound of claim 1 wherein $R_a$ or $R_b$ together with one of $R_c$, $R_d$ and $R_e$ and the carbon atoms to which they are attached form an epoxide.

16. A compound having the structure of Formula (II):

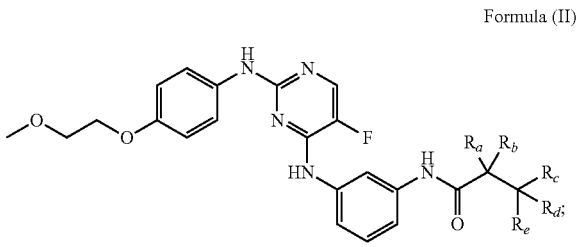

Formula (II)

wherein:
$R_a$, $R_b$, $R_c$, $R_d$ and $R_e$ are each independently selected from H, F, Cl, Br, I, —CN, —$SR_2$, —$OR_3$, —$N(R_3)_2$, and —$CO_2R_3$; or
$R_a$ or $R_b$ together with one of $R_c$, $R_d$ and $R_e$ and the carbon atoms to which they are attached form an epoxide; wherein $R_a$, $R_b$, $R_c$, $R_d$, and $R_e$ cannot all be H;
$R_2$ is selected from H, $C_1$-$C_4$alkyl, a cysteine amino acid fragment, and a glutathione fragment;
each $R_3$ is independently selected from H, $C_1$-$C_4$alkyl, phenyl, and benzyl;
or a pharmaceutically acceptable salt or solvate thereof.

17. A compound having the structure

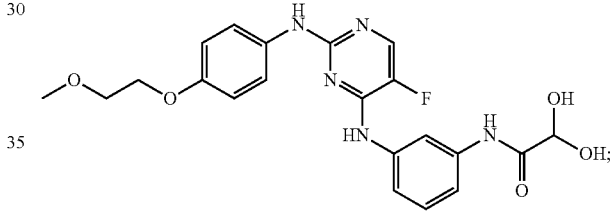

or a pharmaceutically acceptable salt or solvate thereof.

18. A pharmaceutical composition comprising a compound having the structure of Formula (I):

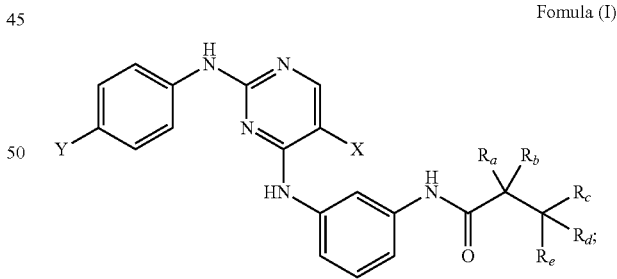

Formula (I)

wherein:
$R_a$, $R_b$, $R_c$, $R_d$ and $R_e$ are each independently selected from H, F, Cl, Br, I, —CN, —$SR_2$, —$OR_3$, —$N(R_3)_2$, and —$CO_2R_3$; or
$R_a$ or $R_b$ together with one of $R_c$, $R_d$ and $R_e$ and the carbon atoms to which they are attached form an epoxide; wherein $R_a$, $R_b$, $R_c$, $R_d$, and $R_e$ cannot all be H;
X is F, Cl, Br, I, or $CF_3$;
Y is F, Cl, Br, or I; or —$OC_1$-$C_2$alkyl optionally substituted with halogen or —$OC_1$-$C_2$alkyl; or an optionally substituted $C_2$-$C_5$heterocycle;

$R_2$ is selected from H, $C_1$-$C_4$alkyl, a cysteine amino acid fragment, and a glutathione fragment;

each $R_3$ is independently selected from H, $C_1$-$C_4$alkyl, phenyl, and benzyl;

or a pharmaceutically acceptable salt or solvate thereof; and a pharmaceutically acceptable excipient, binder or carrier.

19. The compound of claim 1 wherein the compound is in an isolated form.

* * * * *